United States Patent [19]

Storace

[11] Patent Number: 4,669,647

[45] Date of Patent: Jun. 2, 1987

[54] SURGICAL STAPLER

[75] Inventor: Anthony Storace, Norwalk, Conn.

[73] Assignee: Technalytics, Inc., Montvale, N.J.

[21] Appl. No.: 829,755

[22] Filed: Feb. 14, 1986

Related U.S. Application Data

[63] Continuation-in-part of Ser. No. 526,777, Aug. 26, 1983, Pat. No. 4,582,237.

[51] Int. Cl.⁴ .............................................. A61B 17/04
[52] U.S. Cl. ............................... 227/19; 227/DIG. 1; 227/83; 227/155
[58] Field of Search ............. 72/409, 410; 128/334 R; 227/19, DIG. 1, 83, 120, 156, 155

[56] References Cited

U.S. PATENT DOCUMENTS

| | | | |
|---|---|---|---|
| 1,514,259 | 11/1924 | Peters | 72/409 |
| 3,665,924 | 5/1972 | Noiles et al. | 227/DIG. 1 |
| 3,945,238 | 3/1976 | Eckert | 227/DIG. 1 |
| 4,317,535 | 3/1982 | Huftel | 227/19 |
| 4,391,401 | 7/1983 | Moshofsky | 227/DIG. 1 |
| 4,396,139 | 8/1983 | Hall et al. | 227/19 |
| 4,399,810 | 8/1983 | Samuels et al. | 227/19 X |
| 4,411,378 | 10/1983 | Warman | 227/19 |

Primary Examiner—Paul A. Bell
Attorney, Agent, or Firm—Rosen, Dainow & Jacobs

[57] ABSTRACT

A surgical stapler having a pivotable trigger in a housing and a cartridge of surgical staples, has a moving anvil which receives one staple at a time in its open configuration. A forming blade moves to engage and capture the staple between the forming blade and the anvil and drive the staple away from the cartridge allowing the user to see and place the points of the staple at a desired location on the tissue. Further movement of the forming blade pressing upon the top of the staple forces the staple legs to pierce and close joining adjacent edges of tissue. First and second stripper elements acting separately or in combination engage and urge the closed staple to separate from the anvil.

27 Claims, 31 Drawing Figures

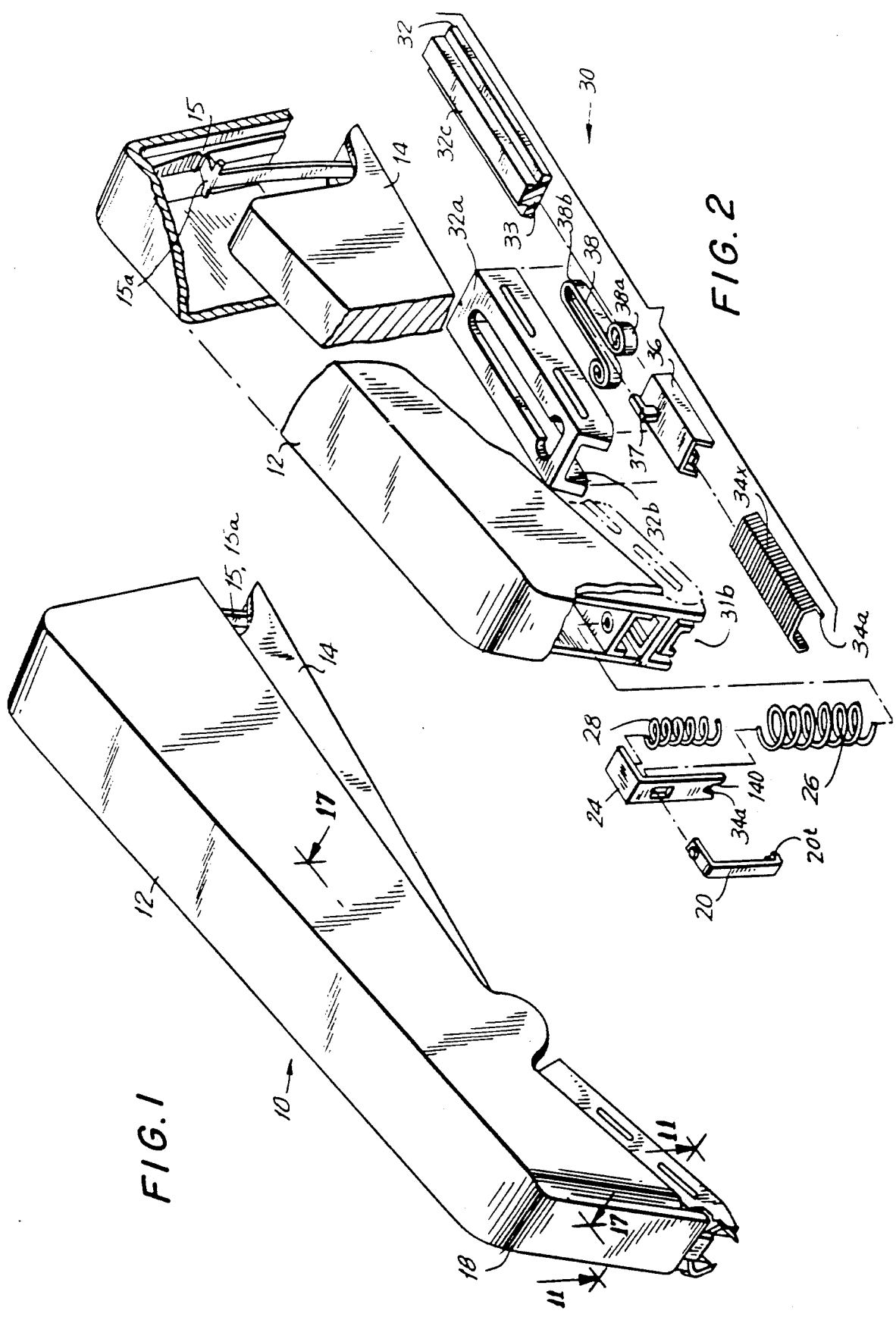

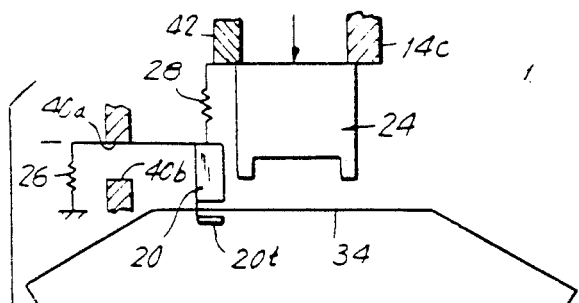
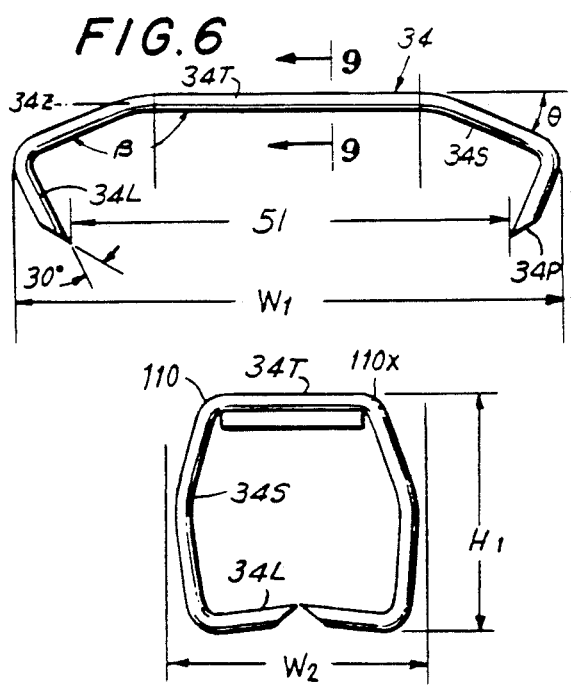
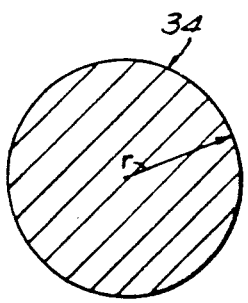
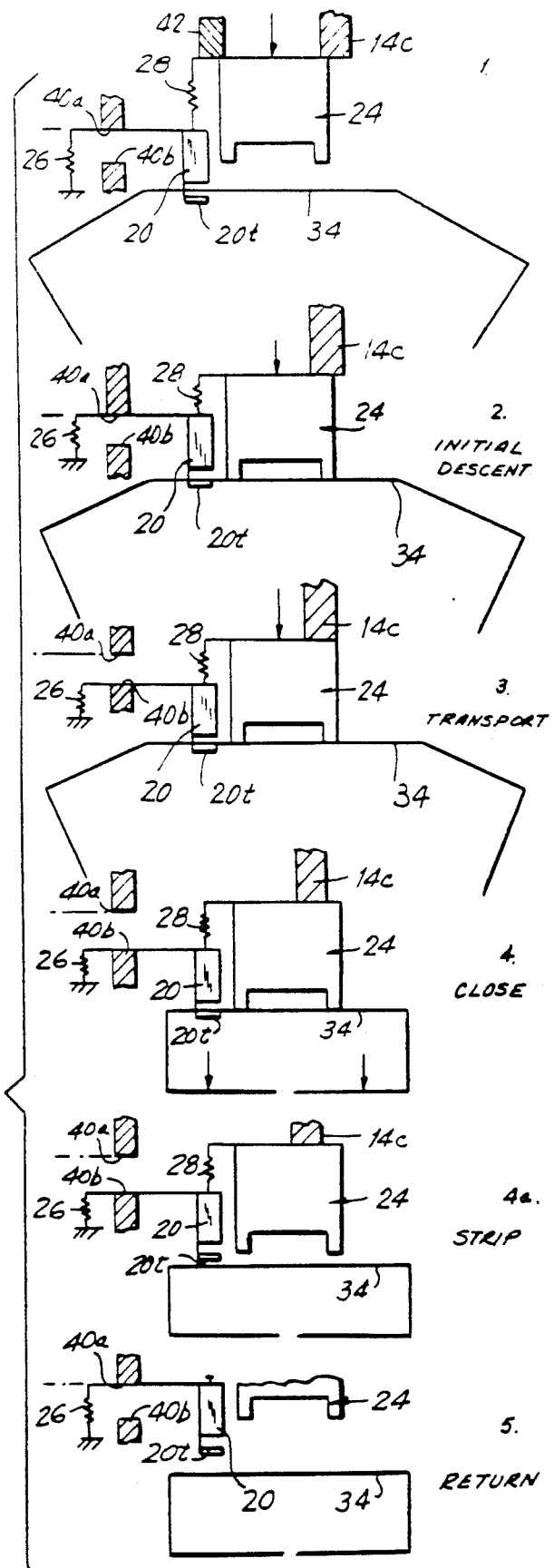

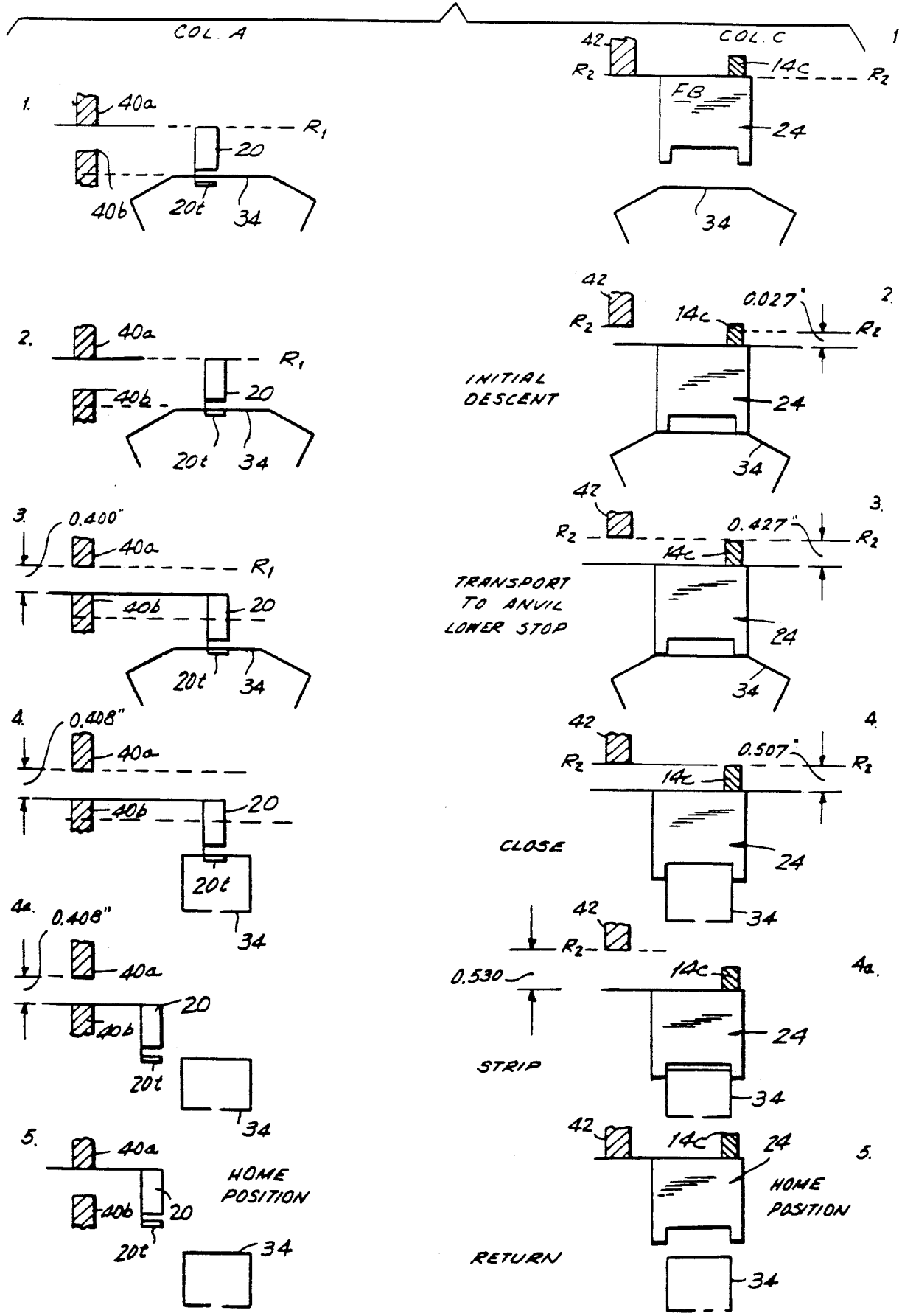

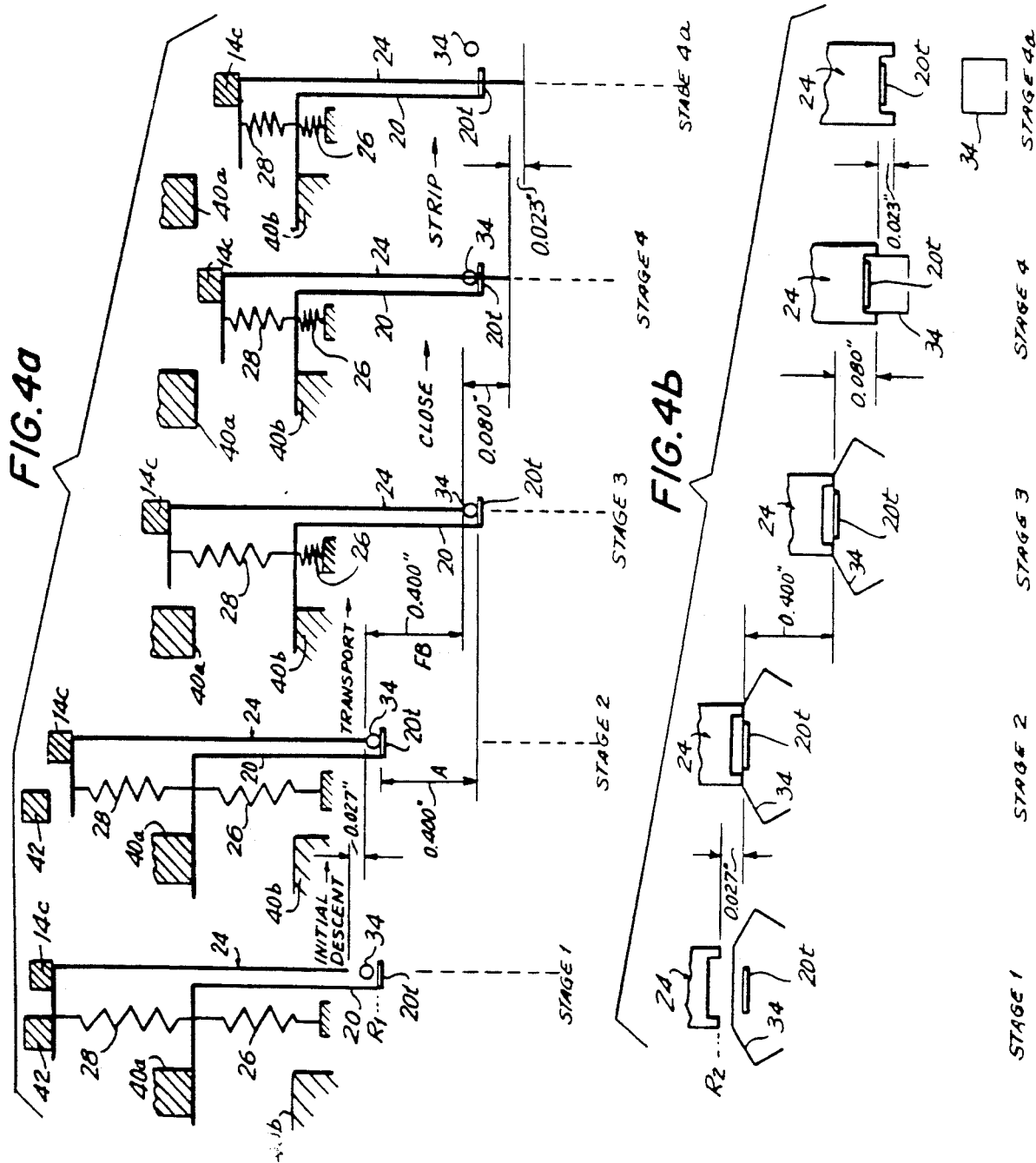

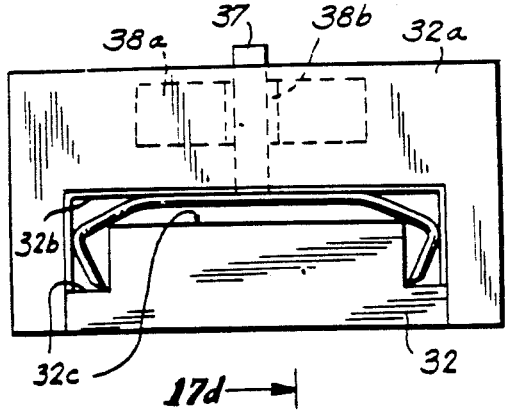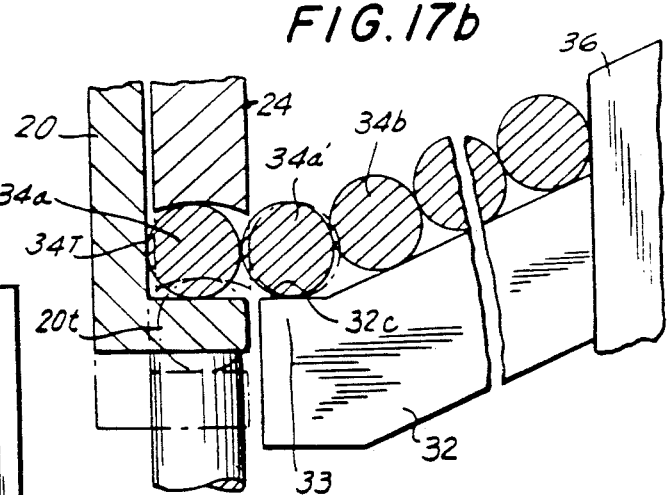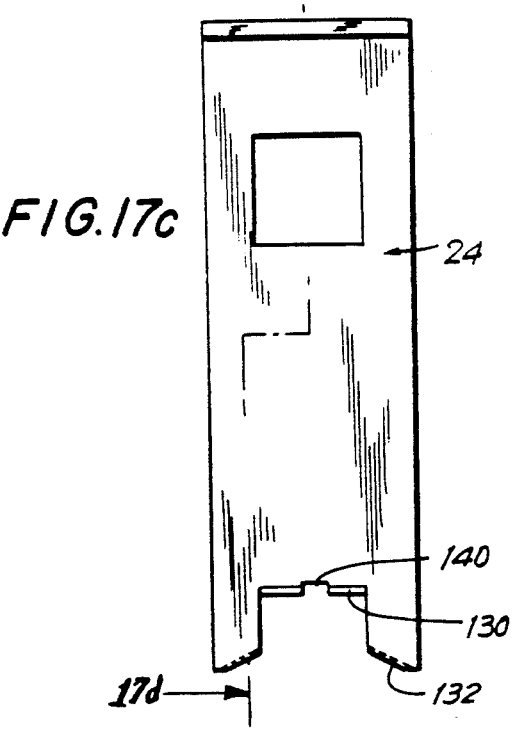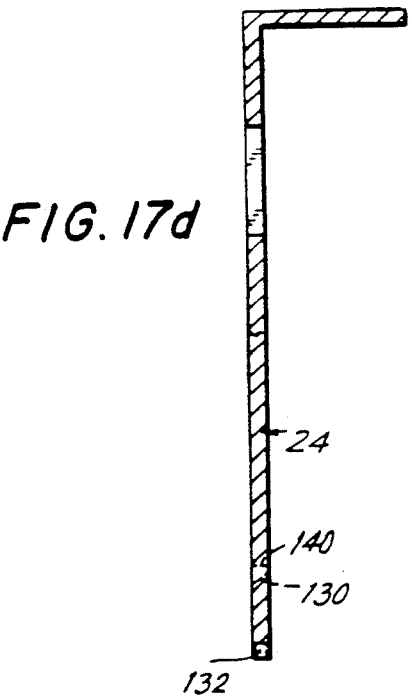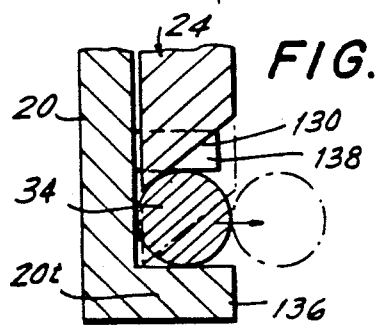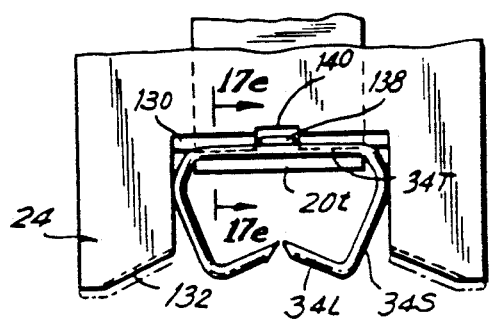

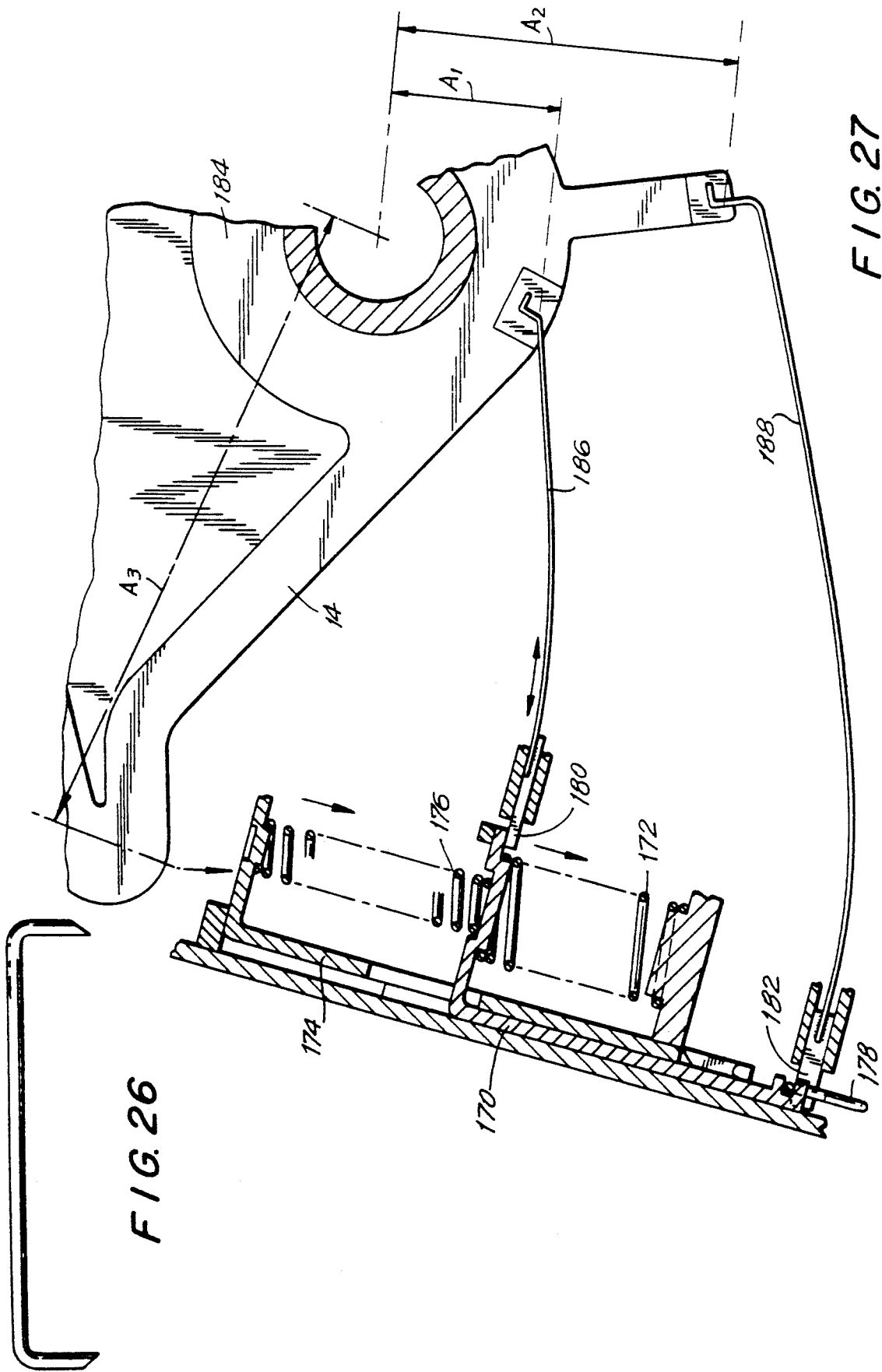

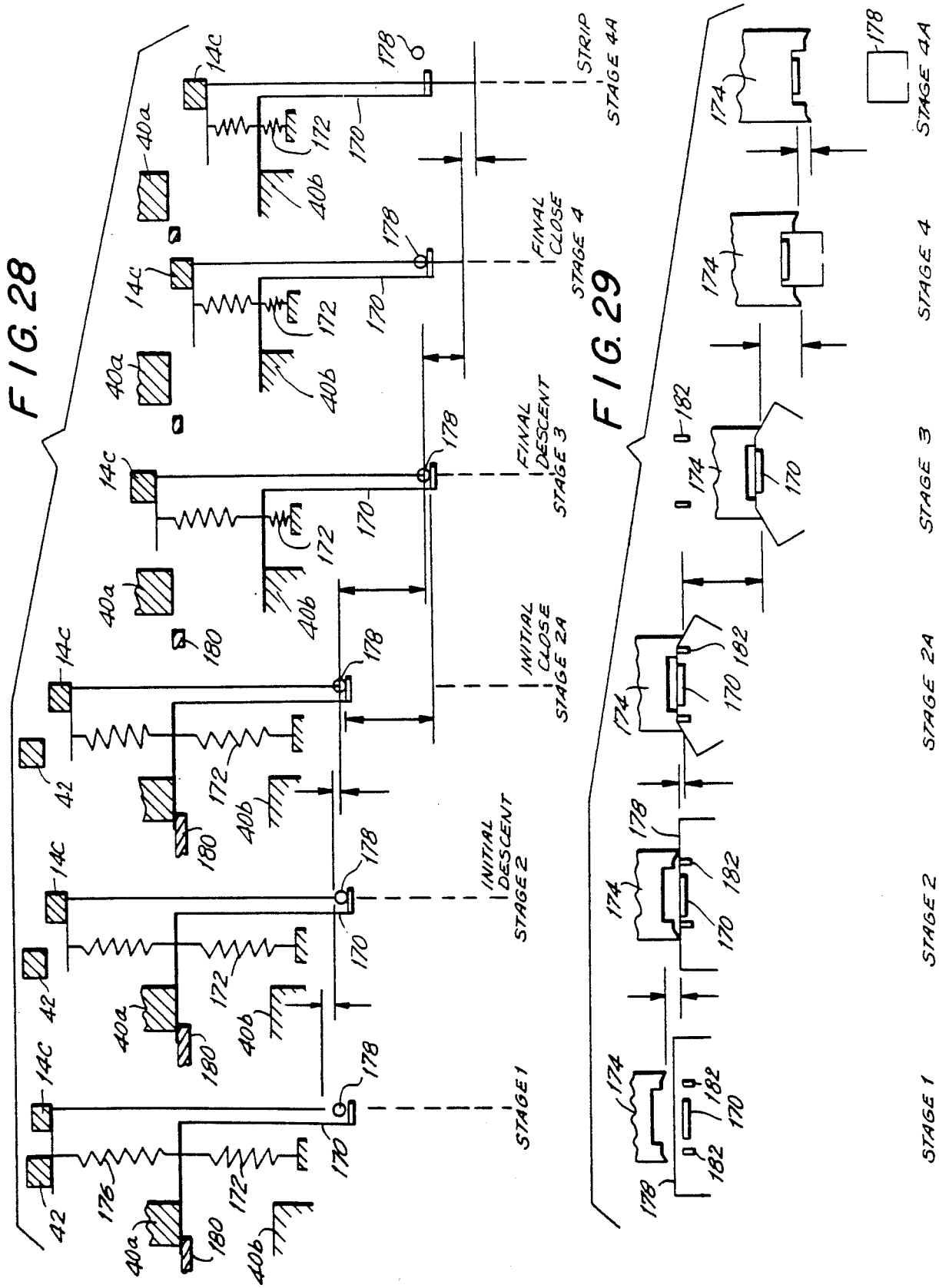

SURGICAL STAPLER

This application is a continuation-in-part of application Ser. No. 526,777 filed Aug. 26, 1983, now U.S. Pat. No. 4,582,237.

BACKGROUND OF THE INVENTION

This invention is in the field of surgical staples and surgical staple guns for implanting such staples. A very large number of surgical stapler devices have been made in the last few years by a growing number of manufacturers; however, in all cases the staples used were essentially conventional stainless steel or equivalent staples, generally similar to those used for stationery products, other packaging or joining equipment. More particularly such staples are preformed in a wide open condition with legs of the staple directed parallel and downward from a top arch or crossbar to grasp adjacent edges of an incision for closure. These staples are contained in a magazine, and each is released one at a time and moved laterally forward to a fixed anvil which supports the underside of the crossbar while its sharply pointed ends engage and pierce tissue and are forcibly bent to close about and capture the edges of the juxtaposed tissue.

In typical prior art staplers the staple is forced from a generally rectangular configuration to generally closed rectangular configuration by applying force at two points on the top side of the staple while restraining it inbetween these points. The term anvil is used because the staple is closed by forcing the legs against a fixed, rigid anvil-like support within or near the surface of the stapler's housing. Such substantial forces are required that the support anvil is traditionally a fixed portion of the housing, which thus results in the staple being implanted and closed while its upper arch part remains in the stapler. This arrangement obviously has a limiting effect on the surgeon's ability to see the stapler and the wound.

In addition to the visibility limitation due to the location of the staple partially within the device during closure, the prior art devices are relatively large to begin with which is another inherent visibility obstacle. The width dimension of the prior art housing, for example, must be at least equal to the width of a staple in its fully open configuration in the staple magazine, plus housing thickness and clearance, this total width dimension being significantly greater than the width of a staple in closed configuration.

SUMMARY OF THE INVENTION

This invention is a new surgical staple and a stapler designed to deliver and implant a plurality of staples, one at a time into a patient's tissue, specifically to engage adjacent edges of an incision or wound and close in a manner to hold together these edges. The staples typically made of stainless steel define a wide angular C-shape with two sharply pointed ends directed generally downward and inclined slightly toward each other when the staple is in open condition. When closed each staple has a generally rectangular shape with the legs directed at each other and optionally inclined slightly upward to provide a highly secure closure.

Principal objectives in the present invention are to provide an apparatus which is extremely simple and reliable in operation, one which is simple and inexpensive to manufacture by having the fewest possible parts that can be assembled rapidly, and, furthermore, one which provides high visibility in the area of the staple discharge from the gun so the surgeon can see the staple as he positions it prior to closure and during closure. The new device closes each staple with ample force to pierce skin consistently and reliably, yet requires less force by hand to do so. When closed the staple has its pointed ends either slightly upward or overlying or at least very close together. Also the invention includes a "feelable" pre-cock position at which point a detent engages and prevents return of the trigger. The surgeon can release his hand while the staple is held in its pre-cock position. Furthermore, the device has a non-directional staple release function; accordingly there is no need to move the gun forward, backward, upward or downward to effect release of the closed staple from the gun.

Basically, this surgical stapler is a hand device with a handle part which is gripped in the surgeon's palm and a pivotal or otherwise movable trigger part which is moved when squeezed by the surgeon's fingers against the adjacent handle. The trigger is an elongated element with a pivot point close to the front end so that movement of one end causes opposite motion of the remote end. A mainspring is situated in the housing to urge a forming element upward to bear against and urge the trigger to a clockwise or open position within the handle. Within the stapler the trigger, driven by the surgeon's hand, is the basic power source which is transmitted through various components to deliver and close each staple.

Also inside the device is a magazine containing a plurality of staples arranged in a generally traditional manner, aligned on a magazine mandrel or core and urged by independent spring means to slide along and then off the mandrel one at a time. Obviously, the device allows only the outermost staple to be discharged to a descending anvil and driver element for descent to the discharge area below the cartridge where the staple is closed. The driver or forming blade and moving anvil comprise a sub-assembly for engaging, stabilizing, restraining, delivering the staple to a lower level, closing and finally releasing the staple. An objective is for the separation of the staple from the staple gun to occur easily, quickly and smoothly without further movement of the gun relative to the wound and without chance of the staple "hanging-up" in the gun. When so closed and released the staple is outside of and partially or totally below the cartridge or magazine and lower portion of the gun.

In our preferred embodiment the new staples are stored in the cartridge in the stapler in partially closed state; the resulting housing thus occupies less width than prior art housings and thus provides improved visibility at the closure area. The staple is delivered to a point below the cartridge that is preferably tapered and narrower than the open staple itself; this feature obviously maximizes visibility.

In the new stapler means are provided on the forming blade for preventing the staple from tipping and rolling out of its generally vertical plane. Associated with the forming blade are stripper means for stripping or prying a closed staple off of the anvil so that the stapler device can be easily and smoothly separation from the closed and emplaced staple.

It should be noted that the design of this stapler requires that the trigger be squeezed from open to closed position through a series of phases during which the staple goes through its complete cycle of: engagement, descent, pre-cock, tissue engagement, pierce tissue of opposed edges of the incision, close, and finally separate from the gun. It is the intent herein that the gun and its trigger move in one consistent direction during the entire staple formation and movement phase. This is logically consistent, adds to overall simplicity of the device, and is helpful psychologically for the user to have a trigger moving in only one direction to complete all phases of the staple manipulation to close. This "forward" motion is reversible until the pre-cock position is reached.

By having the staple positioned below the cartridge and in front of the tapered housing, the surgeon can clearly see precisely where the pointed ends of the legs of the staple will be engaged in the tissue. Not only does the new device permit these totally new and novel operations with staples, it does so with the highest visibility ever achieved because the staple, during these moments of final decision, is fully exposed and essentially out of the stapler while it is held by the staple engaging means.

A further feature of one embodiment of this device is the incline of the staple magazine so that the lower housing will be smaller and allow for greater visibility. As generally indicated, the magazine is aligned along an axis that defines an angle less than 90° with the line of descent of the staple driver. It has been found possible to incline the line of descent of the staples relative to the magazine.

In a preferred embodiment the drive system for engaging, transporting, closing and releasing each staple is basically a handle or trigger with a pivot point nearer to one end such that an approximately 3 to 1 leverage ratio is established, and so that a 20° pivot movement of the trigger's near end by the surgeon's hand will cause the remaining components i.e. the forming blade moves sequentially between its start, engage, transport, close and release or strip positions. Alternative drive mechanisms could include gear trains and cam-follower arrangements for producing linear movement of the staple driver from pivoting or other movement of the surgeon's hand.

As described generally above, each staple goes through engagement, descent, closing and release. In a cam drive system, different cams can easily accomodate these different take-offs while the trigger is pivoted smoothly and/or continuously. In direct drive mechanisms means are provided to allow the trigger's continuous pivoting to cause staple-engaging and forming means to first drive a staple downward from the magazine, and then to close and release the staple. Closing of the staple while it remains at a lower elevation requires an "idling" phase of the anvil while the trigger continues moving. This is accomplished in one embodiment by using relatively soft and hard springs axially, the latter not moving until the former is fully compressed.

A variety of other and specific features are disclosed in the detailed drawings and descriptions that follow of preferred embodiments of carrying out the principles of this new stapler invention.

BRIEF DESCRIPTION OF THE DRAWINGS

FIG. 1 is a front perspective view of the new surgical stapler.

FIG. 2 is an exploded view of the stapler of FIG. 1.

FIG. 3 is a schematic representation of the forming blade, anvil and staple elements in their sequential phases of operation.

FIG. 4 is a schematic representation corresponding to FIG. 3 showing separated sub-assemblies.

FIGS. 4a and 4b show lateral spread views of FIG. 4.

FIG. 5 is a front elevation of a prior art staple in closed state.

FIG. 6 is a front elevation of a new staple in open state.

FIG. 7 is a front elevation of the staple of FIG. 6 in closed state.

FIG. 9 is a typical cross-sectional view of the staple, this taken along line 9—9 of FIG. 6.

FIG. 17a is a front elevation view of the staple magazine.

FIG. 17b shows a detail side elevation view partly in section of staples moving from the magazine to the anvil and forming blade.

FIG. 17c shows a rear elevation view of the forming blade.

FIG. 17d shows a cross-sectional view of FIG. 17c.

FIG. 17e shows a detail view of the stripper of FIGS. 17a and 17c.

FIG. 17f shows a rear elevation of FIG. 17e.

FIG. 26 is a front elevation of a staple in open state as loaded in the stapler embodiment representive in FIG. 27;

FIG. 27 is a fragmentary side elevation of a further embodiment of a stapler;

FIG. 28 is a schematic representation corresponding to a side elevation showing stages of operation of a sub-assembly of a forming blade, anvil and corresponding steps of the stapling embodiment of FIG. 27; and FIG. 29 is a schematic representation corresponding to a rear elevation of the subassembly of FIG. 27 showing the corresponding stages of operation.

DETAILED DESCRIPTION OF THE PREFERRED EMBODIMENT

Figure 19A:
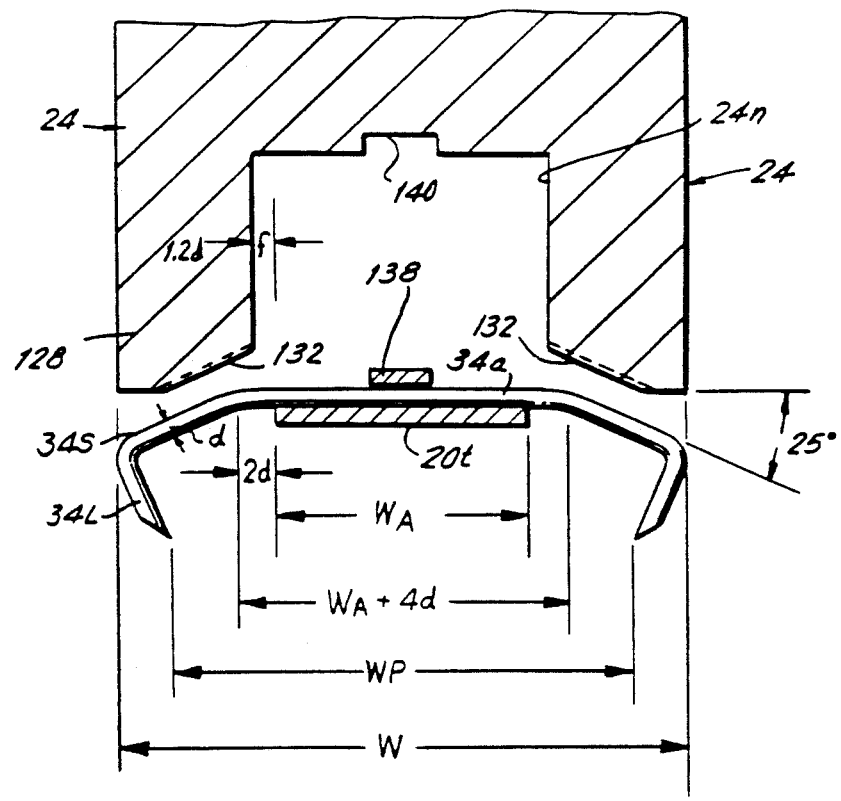
FIG. 19a is a fragmentary sectional view of the staple-forming sub-assembly correspoding to FIGS. 19 and 17f.

The new surgical stapler is illustrated in FIG. 1 showing an assembled device and in FIG. 2 which is an exploded view showing its various principal components. As illustrated in these figures the stapler assembly 10 has a casing or housing 12 with a trigger 14 which is pivotable within the casing about pivot 16, and a detent and spring clip combination 15; 15a provide an audible and/or physical indication that closure of a staple is imminent and to prevent reversibility once engaged. At the front of the stapler is a front cover portion 18 of the casing 12 in the area where staples are discharged one at a time. A cartridge assembly or magazine 30 holds a plurality of staples 34x on a mandrel 32; a pusher 36 driven by a pusher spring 38 urges the staples toward the left as shown. The magazine is inserted into the stapler casing with staples at the front end 33 of the mandrel 32 and front end 32b of the housing of 32a situated near the front opening 31b of the casing. The lead staple 34a of the plurality of aligned staples 34x would be pushed outward into the staple-forming sub-assembly. Generally stated, one staple at a time is discharged into the forming blade anvil sub-assembly which, upon squeezing of the handle, then lowers the staple below the lower front part of the casing. Further squeezing of the handle closes the staple and finally releases the staple from the device, all these phases being illustrated schematically step-by-step in FIGS. 3 and 4.

The staple-forming sub-assembly as seen in FIGS. 2, 19a and 17–17f, comprises the anvil 20 for receiving the lead staple, and the forming blade 24 for driving the staple downward and closing the staple. Anvil spring 26 urges the anvil to its normally upward position, and forming blade spring 28 urges the forming blade also upward relative to the anvil and relative to the casing. An additional feature, particularly shown in FIGS. 17c–17x in the stripper 130 portion of the forming blade which strips or separates a closed staple from the staple-forming subassembly, so that the stapler can be removed from such closed staple which is embedded in a patient's tissue.

The lead staple 34a in the staple magazine is received upon the lower lip 20t of the anvil 20 and subsequently held between said lip and the bottom edge of the forming blade 24. Next the forming blade is driven further downward against the top of the staple's crossbar or arch, which along with the anvil is pushed downward until the anvil is stopped and the forming blade continues its descent relative to the staple which is supported in place by the anvil. As a result, the forming blade forces the partially open leg parts of the staple to be closed for joining and holding adjacent edges of the tissue.

In the cartridge or magazine assembly 30 illustrated in FIG. 2 the staples 34x and pusher 36 slide along the top of mandrel 32 while spring 38 is situated with its ends 38a secured to the front of the mandrel and its mid-part positioned to engage the rear side of the pusher's upward extending tab 37. This spring is preferably a Negator spring applying constant tension regardless of the amount of extension of the spring which will vary depending on the number of staples remaining in the cartridge, to urge the staples off the mandrel in a direction toward the left as shown. The pusher 36 has its own tang (not shown) which projects outward through the housing; the position of this tang indicates the axial position of the pusher and thus the approximate number of staples remaining in the magazine.

The operational phases of the staple-forming assembly are shown schematically in FIGS. 3, 4 and 4a and 4b. The phases are designated 1, 2, 3, 4, and 4a, after which the cycle is repeated as indicated by phase 5. Phase 4A is shown for the strip-off operation wherein the staple is separated from the device. FIG. 3 is a schematic view showing all the principal elements at once which are indicated by reference numerals corresponding to those in the exploded view of FIG. 2 and also at times by suggestive initials. Accordingly, in FIG. 3 there is shown the forming blade FB or 24, the anvil A or 20, the staple 34, the forming blade spring 28, and the anvil spring 26. Also there is an anvil upper stop 40a and lower stop 40b and a forming blade upper stop 42, and the anvil's lower tab 20t for receiving and engaging the lead staple from the cartridge. For convenience of references the anvil's upper stop 40a will also be designated as a basic starting reference plane R1 as a starting plane for the phases. In both FIGS. 3 and 4 the phases are designated 1–4a moving downward from top to bottom.

In FIG. 4 the activities of FIG. 3 have been separated into two columns A and C. More particularly, column A illustrates mainly the anvil 20 and staple 34 as they progress through the five stages; and column C illustrates the forming blade 24 and staple 34 as they progress through the stages. In column A the anvil has its upper stop 40a at reference plane R1 and a lower stop 40b; in column C the forming blade has its upper 40b; in column C the forming blade has its upper position at reference plane R2. At positions 2, 3, and 4 the anvil and/or forming blade have descended downward from their reference planes by distances corresponding to changes and locations of the staple.

Beginning with phase or position 1 seen in FIGS. 3 and 4 and 4a and 4b, the anvil is located in its uppermost position defined by its upper stop 40a. With the anvil in the position, the engaged staple 34 is aligned with the lip or lower tab 20t of the anvil, this staple having been automatically driven laterally into this position by the spring 38 of the magazine (shown in FIG. 2). In moving from position 1 to position 2 the forming blade 24 descends slightly to engage the top of the staple's crossbar while the bottom of the staple's crossbar is supported by the anvil's lower lip 20t. Subsequent downward movement by the forming blade will then be positively transferred by solid contact from the forming blade to the staple and the engaged anvil, thus moving all three parts simultaneously. FIGS. 4a and 4b correspond to FIG. 4 (column A) and FIG. 4 (column C) respectively and provide another perspective of the forming blade-anvil-staple relationship by illustrating a lateral spread of the relative elevation of these elements. During the succession of phases 1–4a discussed above, FIGS. 4a and 4b show the incremental distances moved by the anvil and forming blade between phases, while FIG. 4 shows the cumulative distances moved from the initial reference planes R1 and R2 by these elements.

Figure 14:
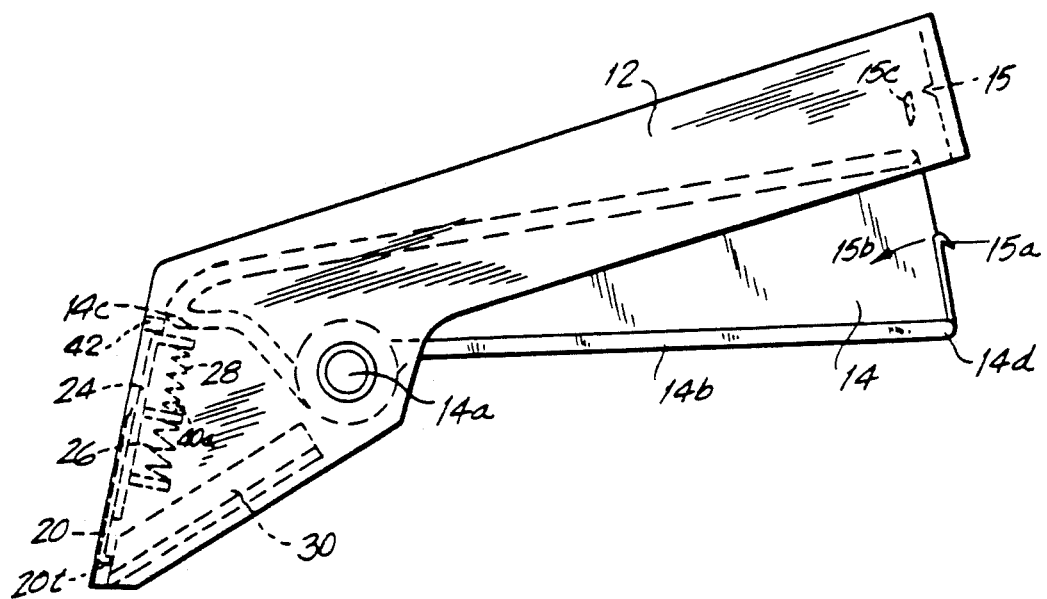
FIG. 14 is a side elevation view of the stapler of FIG. 1.

By appropriate designs of the springs 26 and 28, as seen in FIGS. 2, 3, and 14, the anvil is urged by spring 26 upward at all times relative to the casing, and having its upward motion limited by upper anvil stop 40a. The anvil is also urged toward the forming blade, and a separate spring 28 separates the forming blade from the anvil. When the operation of the stapler device proceeds from position 1 to 2 the staple is captured by virtue of the force of the forming blade applied toward the anvil which effectively sandwiches the staple therebetween, and thus captures it and prevents it from moving out of position or otherwise becoming displaced. The design of the springs is intended to produce about one pound of upward force between the anvil and the staple pushing up while the forming blade is correspondingly pushing down to thus securely hold the staple. It is intended for these elements to be loaded or preloaded in such a way that there is a net "up" force on the anvil, and that in the fully down position there will be sufficient "up" force to pull the forming blade off the staple and overcome the friction between the bottom of the forming blade and the top of the staple resulting after the staple has been bent into a closed position. If there isn't enough force urging the forming blade upward, i.e., if the spring is too soft, then there could be a hangup and the forming blade would in effect stick to the top of the staple and anvil and thus not rise.

A further review of FIGS. 3 and 4 will add certain perspective to the entire process. In FIG. 4, columns A and C the staple is shown initially in its partially closed position which is its shape as aligned on the mandrel in the cartridge 30 of FIG. 2. This staple shape, also seen in FIG. 6, is called herein "open configuration" since this is the staple's initial and most open shape. In phase 2 the forming blade descends slightly as indicated by the 0.027 inches. In position 3 the staple, while still open, has been pushed all the way down because the anvil has hit its lower stop 40b and the staple captured by the lower lip 20t of the anvil cannot descend any farther anyway. At position 4 the staple has been closed, and in position 4a the stripper, as further described below, strips the closed staple from the anvil, although the various elements are at the same elevation as before. At position 5 the anvil has ascended back to the original position leaving the staple closed and embedded in tissue; position 5 corresponds to position 1 so that the next lead staple will automatically be driven onto the anvil's lip 20t.

Column C illustrates how the forming blade moves downward from its reference level R2 in position 1. At position 2 the forming blade has moved an amount indicated 0.027 inches as shown in the drawing. At position 3 the forming blade is down 0.427 inches, at position 4 the forming blade has been driven another 0.08 inches to 0.507 inches in order to close the staple as shown, and by position 5 the forming blade has risen back to its reference position R2.

The basic concept as described earlier includes use of a staple magazine or cartridge within the stapler housing where the magazine holds a plurality of staples in partially closed condition called "open configuration"; one staple at a time it taken off the magazine, carried downward outside of the housing, caused to have its pointed ends pierce tissue, forced to bend to its closed condition, thereby being inserted in and gripping the tissue, and finally released from the stapler device.

In the preferred embodiment, a particular staple construction is used along with a staple delivery system as follows. FIG. 6 illustrates new generally symmetrical staple 34 in its initial "open" configuration whose crosssection seen in FIG. 9 is essentially round along its full length, i.e., along the crossarm or arch 34a, the sides 34b, and the legs 34c, except for the points 34p. The points 34p are cut, sheared or ground at an angle of approximately 30° to insure maximum point sharpness. In the preferred embodiment the dimensions referred to in FIGS. 5–9 are W1=0.555", 0=25°, W2=0.25" r=0.03", H1=0.173".

In the staple magazine the staples are aligned on a mandrel generally in the partially closed position seen in FIGS. 2, 6 and 17a which results in a delivery system being narrower than conventional systems, thereby contributing to improved visibility for the surgeon. As evident in FIG. 6 there is a gap 51 between the points 34p of the staple to allow a blade or stem of the mandrel to extend downward through the gap and be secured to the remaining part of the magazine.

FIGS. 2, 8, 17a and 17b illustrate the staple magazine and its operation. The mandrel 32 has an upper housing 32a with inner grooved surface 32b which helps guide the line of staples. The top surface 32c of the mandrel similarly guide the bottom and inner surface of the line of staples. As drawn the staples hang generally vertically relative to the inclined mandrel, and the lead staple 34A exits the mandrel off generally horizontal lip 33 and onto anvil lip 20t.

FIGS. 11, 17, 17a–17, 19 and 19a further illustrate the staple delivery sub-assembly comprising the anvil 20 and the forming blade 24 in their relative positions. The anvil 20 has a generally vertical blade part with a lower lip 20t projecting rearwardly from the anvil blade into the plane of a staple 34. The anvil moves between upper and lower stops respectively fixed to the stapler housing as indicated in FIGS. 3 and 4. In the upper position the lower lip 20t of the anvil is positioned directly below the staple's crossbar or arch 34t as seen in FIG. 17b. The anvil spring 26 urges the anvil toward its upward position against stop 40 until the anvil is driven down in the staple delivery cycle.

When the anvil is stopped by the lower anvil stop, the forming blade overrides the interposed spring 28 and forces the staple sides 34s or top part 34t to bend around the ends of the anvil lip 20t and forces the legs 34l downward to pierce the skin. The spring 28, interposed between portions of the anvil and forming blade, serves as a return spring for the forming blade urging it upward, as well as being an override spring which allows the forming blade to continue moving downward after the anvil 20 has moved to its lower position where its movement is restrained by the second or lower anvil stop.

FIG. 14 illustrates generally the stapler housing 12 in which the trigger 14 pivots about axis 14a. The trigger is pivoted by squeezing its gripping surface 14b, thus driving it in a counterclockwise direction and thereby urging its front end 14c to drive the forming blade 24 downward. As shown, the anvil return spring 26 is stronger than interposed spring 28 between the forming blade and the anvil. Accordingly, pivoting of the trigger will cause the forming blade alone to descend initially; thereafter the forming blade and anvil will descend together, but by then the staple will be positively captured between them. At the bottom of the anvil's stroke, when it hits its stop 40b, the forming blade will then be driven further, overcoming its own return spring 28 as the staple is closed. The pivot point 14a of the trigger is situated much closer to the forming end 14c of the trigger than the hand end 14b, thus providing a ratio greater than unity and a force advantage that allows the surgeon to deliver and form a staple with only a moderate amount of effort applied by his hand and fingers to the stapler handle. FIG. 14 also shows symbolically the staple cartridge 30 positioned to deliver one staple at a time to the anvil. The last few degrees of motion of the forming blade cause the staple to be stripped.

Figure 19:
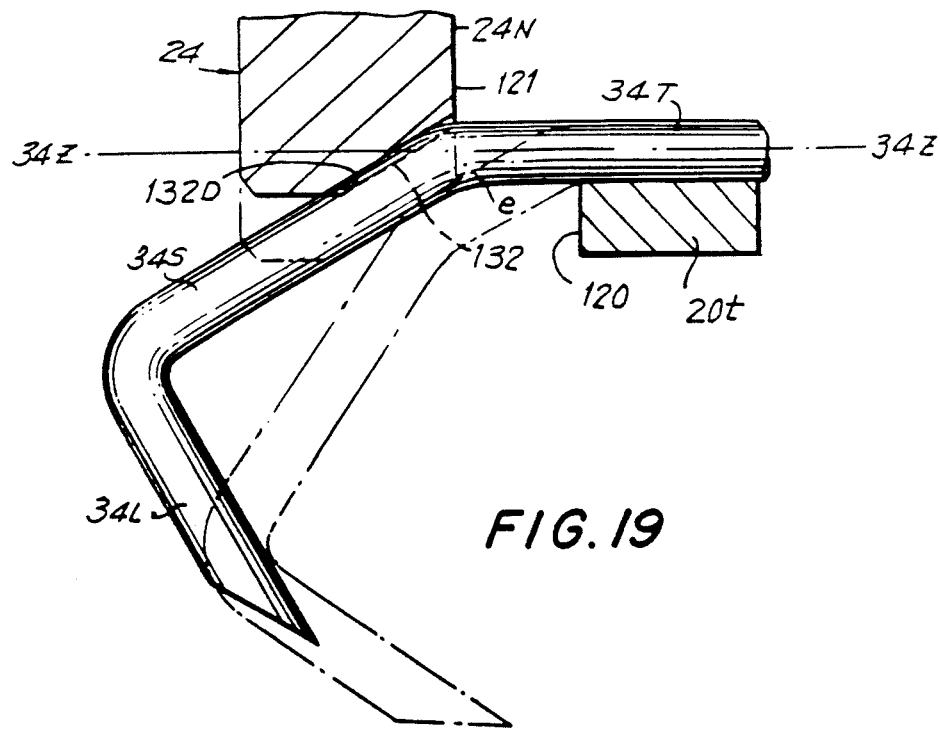
FIGS. 19 and 20 are fragmentary front elevation views showing a staple in open, partially closed and fully closed states.
Figure 20:
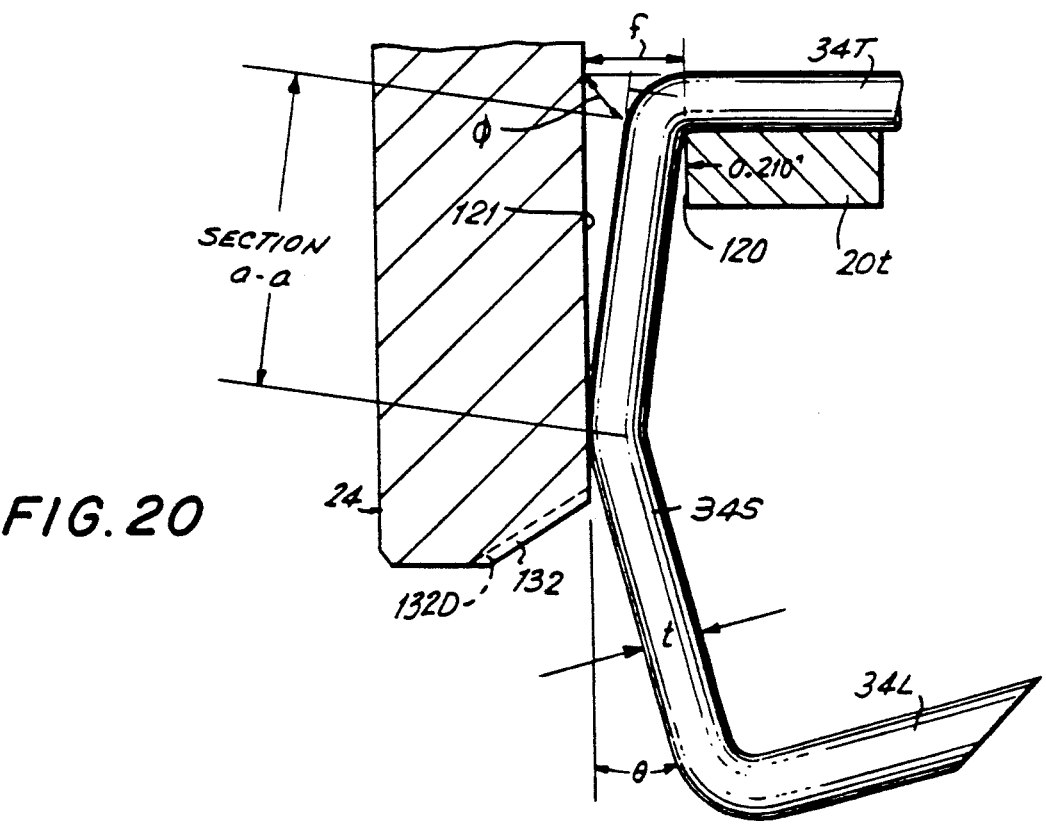
Figure 21:
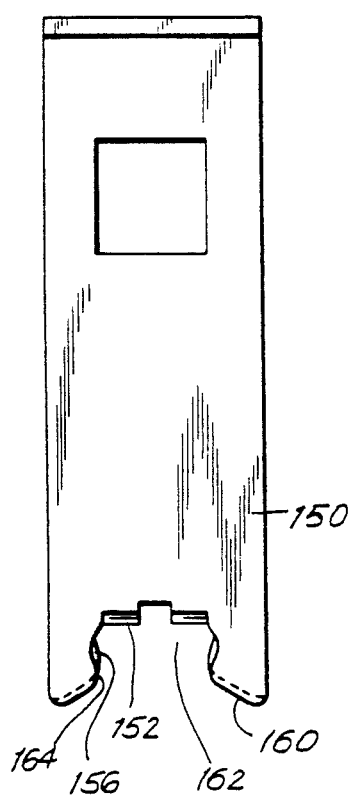
FIG. 21 is a rear elevation of a further embodiment of a forming blade.

The actual closing of the staple by bending the opposite legs 34l is illustrated in FIGS. 19 and 20 as follows. When the staple is closed deformation occurs in the area marked "e" essentially because the anvil has a transverse dimension, in this case 0.210 inches which is substantially less than the original length of the horizontal crossarm 34t of the staple. During closure of the staple in the course of surgical insertion, the staple is closed by the forming blade which changes the staple from that shown in FIG. 6 to FIG. 7. The space on each side between the edge 120 of the anvil (FIGS. 19 and 20) and the adjacent inner edge 121 of the forming blade tang results in a gap within which the staple is bent. This gap, $f$ in FIG. 20, is larger than the thickness of the staple $t$; in the embodiment shown $f = 1.2t$. The dimension $f$ is significant because it represents the space allowed for the bent staple to exist; the more the staple is bent, the greater will be the friction between the two edges defining dimension f, and the more difficult it will be to effect closure and also the more difficult it will be to lift the forming blade away from and disengage from the staple which will be trapped between it and the anvil.

The prior art surgical staplers require approximately 55 lbs. of force to effect the bending because they have to bend essentially 90°, and this necessarily means that dimension f will be very small, in fact less than t, and the friction will be extremely high. In the present invention the force of only 18 pounds is required to achieve full closure or even to achieve overcrimping, i.e., closure until the staple legs are bent to the orientation illustrated in FIGS. 7 or 20, 17f, or even greater ones crimp shown in FIG. 17f.

FIG. 19 illustrates a staple in its initial open phase 1 and an intermediate bent stage; FIG. 20 shows the staple in its final closed phase 4a. Also shown are the corresponding position of the forming blade and the groove 132 in the forming blade which engages and guides the staple from tipping or rolling about any longitudinal axis 34Z extending through the crossbar. Point 132D of forming blade 24 is lower than axis 34Z and the engagement of point 132D on the staple's side 34S stabilizes the staple from rolling or tipping about axis 34Z.

As the forming blade bends the staple around the corner of the anvil, the section of the staple between the corner of the anvil and the upper staple (Section a—a FIG. 20) corner rotates through an angle $\phi$ shown in FIGS. 19 and 20. Due to the angle $\theta$ (see FIG. 6) between this section and the lower leg of the staple, the lower leg is rotated approximately 25 degrees ahead of the section a—a (see FIG. 20). Thus, to force the point of the staple to rotate to a horizontal attitude requires a rotation $\phi$ of less than 90° of the staple leg. A rotation of approximately 65 degrees will result in horizontal staple points, thus the dimension f in FIG. 20, which for a conventional stapler must be no wider than the wire thickness to ensure full rotation of the point, in this invention can be larger than the wire thickness (typically 1.2t). This results in a substantial reduction in the force required to close the staple which has important ramifications in other areas of the design. By reducing the dimension f, the points of the staple when fully closed can be made to touch or cross providing overcrimp which significantly improves the staple's reliability of piercing the skin and thereafter remaining securely emplaced. Overcrimp means a staple configuration wherein the staple ends point slightly upward or overlie each other rather than merely point co-axially at each other while separated.

Figure 11:
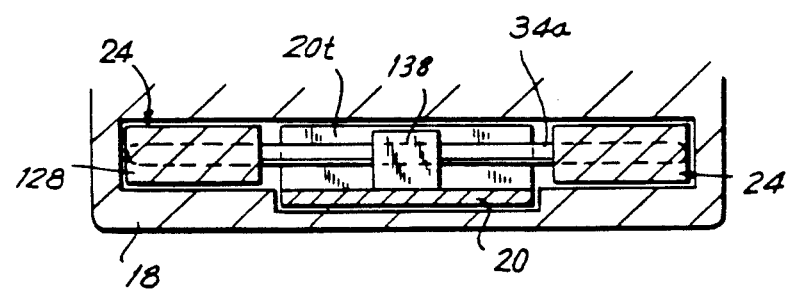
FIG. 11 is a fragmentary sectional view taken along 11—11 of FIG. 1 of the staple-forming sub-assembly.
Figure 17:
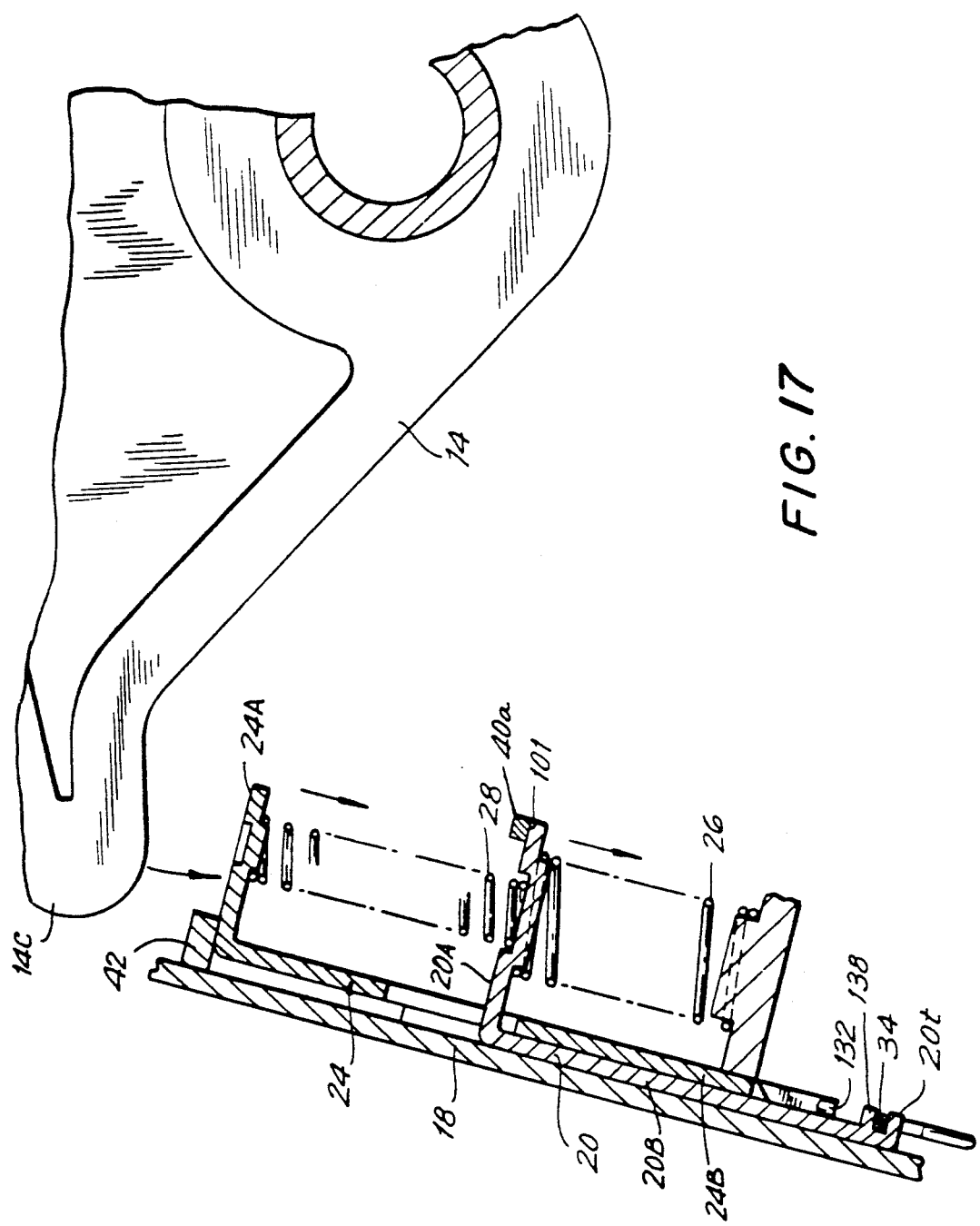
FIG. 17 is a fragmentary sectional view taken along line 17—17 of FIG. 1 of the staple-forming sub-assembly.

FIG. 11 is a sectional view corresponding to FIGS. 17 and 19a, showing the lateral relationship of the anvil, forming blade and front edge 18 of the housing. In FIG. 19a the anvil lip 20t has width WA; W is the width of the open staple; WP is the width between staple points; d is the staple wire diameter; and 1.2 d is the gap f between the anvil lip edge and the side wall 24N of the notch of the forming blade. Upon descent of the forming blade the staple is bent and the staple legs lie in the gap space.

The previously described detent and spring clip combination 15, 15a or equivalent device, provides an audible and/or physical indication that handle movement has progressed a predetermined amount and the staple is in its lowest position ready for final closure. A second audible signal may be provided and indicate that closure has occurred, i.e., that the staple is fully closed and released from the device. Accordingly, with this feature the surgeon will know when he can still release the handle, return the staple to the gun and attend to other matters prior to re-using. To an extent this apparatus is reversible in that the springs within the housing urge the pivoted handle to return to its open position.

The stripper feature referred to earlier allows smooth and quick separation of the stapler from a staple after closure is complete and the staple legs are embedded in a patient's tissue. As indicated in FIGS. 3 and 4 stripping occurs between phases 4 to 4a, whereby the staple's crossbar is cammed off the anvil's lip. Details of the stripper are seen in FIGS. 17c–17f wherein the forming blade's lower edge 130 is bevelled about 30°, while adjacent outer parts 132 are grooved concavely. During initial phases of closure the forming blade's grooved edges 132 engage and partially capture the top outer edge of the staple's crossbar, such capture preventing the staple from "rolling" out of its essentially vertical plane. Rolling or tipping of the staple is not uncommon in prior art staples when the staple points meet resistance to penetration or when the user inadvertently moves the stapler transversely off the plane of the staple while the points have penetrated tissue and the crossbar is still secured to the anvil.

After forcible descent of the forming blade relative to the anvil causing full closure of the staple's legs, slight additional trigger movement causes final descent of the forming blade relative to the anvil whereby the bevelled edge 130 in FIGS. 17e and 17f cams the staple's crossbar 34T off the anvil's supporting lip 136. This simple finger movement on the trigger affects full release of the staple with no requirement of the surgeon moving his hand or the stapler laterally forward or backward and no danger of the staple being "hung-up" or otherwise stuck in the stapler. The stripper action also assures separation despite any tendency of the staple to remain engaged to adjacent edges 121 of the forming blade which previously forced the staple into its final configuration, especially after release of the handle. The exact angle of the bevelled edge 121 may vary depending on the diameter and cross-section of the staple's crossbar, and the amount of trigger motion one desires for stripping versus the speed of stripping, a greater angle obviously requirement more motion but less force.

A further embodiment of the stripper is shown in FIGS. 21–25. Here the forming blade 150 has the stripper bevel 152 for camming the closed staple's crossbar 154 off the lip 153 of the anvil 155, as generally described earlier, and a pair of angled release surfaces 156 for camming or nudging the elbows 158 of a closed staple. Surfaces 156 are located a distance K in FIG. 22 from bevel 152 which corresponds to the distance K' between the closed staple's elbows 158 and crossbar 154. After the forming blade descends and closes the staple bevel 152 begins its stripping phase and essentially at the same time surfaces 156 will nudge the staple's elbows transversely rearward out of the plane of the forming blade. Accordingly, the closed staple is cammed by bevel 152, and the staple's elbows are cammed by surfaces 156, so that the staple essentially falls free of the stapler with no requirement of transverse or upward motion of the stapler by the surgeon to effect complete and quick separation of the stapler from the closed staple embedded in a patent's tissue.

During the staple's transport and closing phases, immediately prior to the stripping phase, the forming blade's lower guide grooves 160 engage the top of the staple's side and, as described above, stabilize the staple from tipping or rolling while it is captured between the forming blade and anvil and is transported (lowered)

and closed. As the closure phase proceeds, as seen in FIG. 19, the staple's sides bend from the position shown in solid line to the position shown in dotted line, during which time the grooves 132 engage, guide and stabilize the staple from rolling or tilting. During further closure from the configuration seen in FIG. 19 to that of FIG. 20, the staple sides leave contact with grooves 132 and slide along the inside wall surface of the notch opening 121 of the forming blade in FIG. 20 corresponding to wall 156 of opening 162 in FIG. 23. Subsequently, during the stripping phase in the FIG. 23 embodiment, the pair of release surfaces 156 come into engagement with the staple's elbows 158 which become quickly released from their frictional engagement with side walls 156; with simultaneous stripping of the crossbar, full and free release of the closed staple results.

The anvil is provided with an anti-bowing tang 138 seen in FIGS. 17e and 17f to prevent the crossarm of the staple from bowing upward when the legs are bent downward. The forming blade has a corresponding recess 140 to allow space for tang 138 on the forming blade's descent. Bowing of the crossarm is undesirable, because such would be a distortion of the intended final configuration and result in less effective closure security.

FIG. 17b shows details of the staple cartridge where the mandrel 32 is inclined downward about 45° and has a lead edge 33 as a generally horizontal lip, so that the lead staple 34A approaches the anvil's support lip 20t aligned therewith instead of inclined thereto as seen in FIG. 17b. The preferred form of mandrel shown in FIG. 17b tends to avoid the drawing down of the number two staple 34A' by the descending forming blade immediately after the lead staple is picked up by the anvil.

In concluding, a number of features will be summarized and/or redescribed from a different perspective. Because the stripper cams the crossbar of a closed staple off the anvil lip by virtue of continued squeezing of the trigger, the closed staple is disengaged from the gun in an essentially non-directional manner. More specifically, the surgeon is not required to move or urge the staple gun in a particular lateral, vertical or inclined direction relative to the engaged tissue to achieve disengagement. It is further noteworthy that this stripper is integral with the forming blade, so that no additional parts are required to be made or assembled. The staple magazine is normally attached to the lower front of the housing by an upward movement into the recess provided. As seen in FIG. 17a the line of staples is guided between the surfaces 32b and 32c.

A key feature of this new device is the descending anvil which receives and guides the staple downward and then supports and stabilizes it during closure. Additional stabilization is provided by the forming blade and the housing. A principal benefit of having the staple lowered below the housing before closure is that the staple may be essentially fully visualized from in front, above and beside the gun before and during closure.

The detent feature illustrated in FIG. 14 allows the trigger to move reversibly until detent 15a which is spring biased leftward in the direction of arrow 15b, is cammed rightward by cam 15c forcing detent 15a to engage projection 15. After this engagement the trigger cannot reverse, but can only continue, which helps prevent a double staple feed and resultant hang-up. Upon full squeezing of the trigger and full closure and release of the staple, release of the trigger leads the resilient detent to return by and be cammed forward by cam 15c so that detent 15a and projection 15 will not engage. Later, upon repeat of the cycle detent 15a is again cammed rearward to engage element 15.

The stapler described above has been shown as used with a staple which is loaded and carried in a partially closed configuration as seen in FIGS. 2, 6, 3, 4, 17a, 19, et. It is possible in another embodiment, shown in FIGS. 27–29, to use conventional staples which initially have the typical prior art rectangular shape seen in FIG. 26 and in FIG. 29 (stages 1 and 2), which is the shape in which these prior art staples are loaded and carried by the stapler. After the "initial descent" in this new embodiment, where the forming blade makes contact with the staple already upon the anvil, the forming blade will continue descent whereby it "partially" closes the staple to the shape seen in FIG. 6 and in FIG. 29 (stages 2A and 3). Such partial closure may occur before or after the "initial descent" phases, as will be explained in further detail later. Upon completion of initial descent, the anvil reaches its lower stop, and closure of the staple follows generally the procedure set forth with regard to the above-described first stapler embodiment.

In order for the staple to be bent from the open rectangular shape of FIG. 26 to partial closed state of FIG. 6 or FIG. 29 (stage 2A), the anvil must be temporarily restrained from descent while the forming blade descends slightly. Such temporary restraint can be achieved in a number of ways, two of which are: (1) using anvil and forming blade springs of a specific mutual relationship and (2) using a removable, second anvil stop.

As shown in FIGS. 4a and 17 the anvil 20 has an anvil spring 26, and the forming blade 24 has a forming blade spring 28. Initial descent of the forming blade until it contacts the top of the staple on the anvil, compresses only the softer or weaker forming blade spring 28, while the stronger anvil spring 26 continues to urge and maintain the anvil up against its upper stop 40a. Next, during the transport phase, the anvil spring 26 compresses, allowing the anvil to descend. In the further embodiment shown in FIGS. 27–29, the anvil 170 should remain "up" momentarily while the forming blade 174 descends slightly, during which time the open prior art type rectangular staple 178, also shown in FIG. 26, is partially closed to a configuration approximating that of FIG. 6.

The sequence of phases or stages for transport, closure, and release of the prior art type staple in the new stapler is shown in FIGS. 28 and 29 which correspond closely to FIGS. 4a and 4b, except for differences explained below. Stages 1 and 2 are the same, respectively, for delivery of a staple to the anvil at its up position and descent of the forming blade to merely contact the staple upon the anvil lip. Added structure in this embodiment shown in FIGS. 27 and 29 comprises: (a) a movable anvil stop 180 and (b) movable staple support pins 182. The anvil stop 180 maintains the anvil at its up position even as the forming blade is driven downward slightly, as seen in FIGS. 28 and 29 to bend the staple from rectangular to partially closed state. The pair of staple support pins 182 below the staple are generally aligned with the anvil lip. These pins establish the bend points 184 where the staple sides bend into the shape indicated at stage 2A, FIG. 29.

During Stage 3, further pivoting of the trigger 184 pulls anvil stop 180 from beneath the anvil arm and pulls pins 182 from beneath the staple, and drives the forming blade further downward, thus transporting the staple and anvil to the anvil's lower stop 40b. Pins 180 are shown withdrawn in FIG. 29, Stage 3. Stages 4 and 5 are essentially the same as in FIGS. 4a and 4b.

In FIG. 27 the anvil stop 180 and pins 182 are pulled by lever arms represented by A1 and A2 respectively of trigger 184. The dimensions of these arms are determined with respect to lever arm A3 for driving the forming blade, such that stop 180 and pins 182 move at the appropriate time with respect to the desired descent of the forming blade 174. After being moved during Stage 3, stop 180 and pins 182 later return to their starting positions by reason of spring resiliency in links 186 and 188 respectively or by other spring or non-spring means, as the trigger pivots back clockwise.

As an alternative to the added structure of stop 180, the anvil spring 172 and forming blade spring 176 could be designed with stiffnesses and relative stiffnesses (not shown), such that during stage 2A when the anvil is to remain at its Up stop position while the forming blade descends slightly to partially bend the staple, the anvil is maintained in its Up position by the stiffness of the anvil spring. Next, during further descent of the forming blade in Stage 3, the force of the forming blade overcomes the anvil spring's stiffness. Pins 182 would be used as before.

Figure 22:
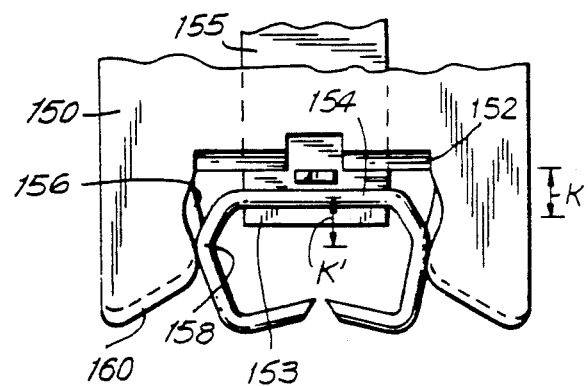
FIG. 22 is a fragmentary rear elevation of the forming blade of FIG. 21 with a staple during the closure stage.
Figure 23:
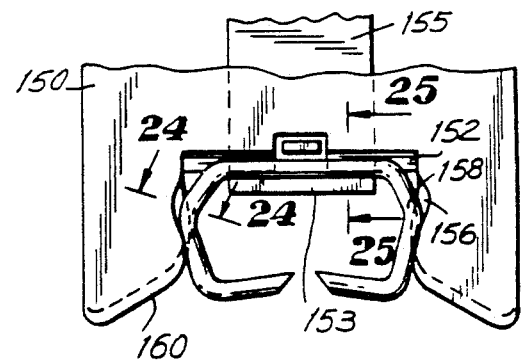
FIG. 23 is similar to FIG. 23 with the staple during the stripping stage.
Figure 24:
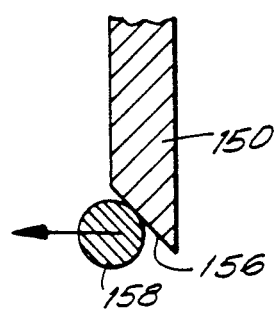
FIG. 24 is a fragmentary sectional view taken along line 24—24 in FIG. 23 showing part of ths stripping stage.
Figure 25:
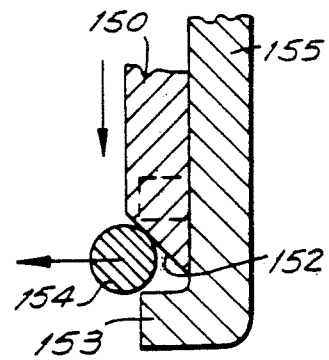
FIG. 25 is a fragmentary sectional view taken along line 25—25 of FIG. 23 showing part of the stripping stage.

Preferred embodiments of the subject invention may comprise a number of different combinations of features as will be described below. As seen in FIG. 22, a stapler may have the side stripper 156 in addition to the top stripper 152 for camming a closed staple off of the anvil. Alternatively, a stapler may have the side stripper alone while the mechanism is designed for use with staples that are loaded in a partially closed state of FIG. 46 or staples in a fully open state of FIG. 29. In the latter case each staple is first partially closed by the stapler, then lowered, and then fully closed and stripped off the anvil. For convenience of terminology in both cases, the staple in its initial state may be characterized as "open" even though in FIG. 4b it is partially closed in initial stage 1 with the legs of the staple extending downward and converging and in FIG. 29 it is fully open in stage 1 with the legs extending merely primarily downward.

It should also be noted that while these two figures refer to specific "stages", "1", "2", etc. which are described in detail in prior sections above, the forming blade and staple may be deemed, for covenience in terminology to be operated through a first period or first stage comprising a number of phases during which time staple is bent from "open" to "closed" state and moved downward, and through a second period or stage during which time the closed staple is stripped off the anvil. Accordingly, as defined in claim 4 below, during such first stage, there are three sequential phases, namely, a first phase for bending the staple from open to partially closed state, a second phase for driving the anvil and staple to a second position displaced from the first, and a third phase for bending the staple to its fully closed state.

The stripping stage not only separates or cams a closed staple off the anvil, but does so while the stapler remains essentially unmoved except for the slight stripper motion. In these embodiments the closed staple is cammed in a direction transverse or optionally perpendicular of the direction of movement of the forming blade or of the plane of the staple. As shown, the staple is driven in a downward direction with respect to the stapler in upright orientation; however, the staple when moved may be directed in directions other than downward.

The side stripping element 156 as shown comprises merely an upward extending recess in the forming blade's drive surface defining spaced side walls joined by a top wall, with a portion of each side wall formed as an inclined or bevelled edge relative to the direction of movement of the forming blade. The inclination of the bevel of this side stripper and of the top stripper is in the range of 20° to 70°. An alternative form of side stripper not shown would comprise an element separate from the forming blade but coupled to the trigger for operation in appropriate timing with the forming blade.

The various stapler embodiments disclosed herein comprising various combinations of the elements and submechanisms described are presumed to operate cyclically with a plurality of staples carried by the stapler housing; however, each stapler can also operate with a single staple combined with the stapler or loaded into an otherwise complete stapler apparatus.

The invention described herein has focused upon certain preferred embodiments and features; it is intended, however, that numerous variations and equivalent embodiments be considered within the spirit and scope of the invention as set forth in the appended claims.

I claim:

1. A surgical stapler operable with a staple that is bendable from an open state which in upright orientation has a horizontal crossbar and generally downward extending pointed legs to a closed state with the legs pointed generally toward each other, the stapler in upright orientation comprising a housing, first means for holding at least one staple in said open state in said housing, an anvil at a first position for receiving a staple from said first means and supporting the crossbar of said staple, a forming blade movable downward through a first stage from start to closure positions and subsequently through a second stage from closure to strip positions, and second means for driving said forming blade through said stages, said forming blade comprising a body part having a lower portion comprising a drive surface which defines therein an upward extending arched recess having spaced apart side walls joined by a top wall, said side walls each comprising at least in part a first edge inclined relative to said downward direction, whereby, during movement of the forming blade through said first stage while said anvil remains stationary said drive surface engages and bends a staple about said anvil to said closed state thus forming sides of the staple between its crossbar and legs, and whereby, during movement of said forming blade through said second stage while said anvil remains stationary said inclined edges cam said sides of said staple in a direction transverse of said downward direction, thereby stripping said staple in closed state off of said anvil.

2. A stapler according to claim 1 wherein said first inclined edges cam a staple in closed state in a direction generally perpendicular to said first direction.

3. A stapler according to claim 1 wherein said staple in open state and upright orientation comprises a horizontal crossbar and legs which extend generally vertically downward therefrom.

4. A stapler as claimed in claim 3 wherein said staple has a partially closed state wherein said legs are directed to converge toward each other and wherein said forming blade has first, second and third sequential phases of movement during said first stage, said forming blade during said first phase bending said staple from open to partially closed state while said anvil remains stationary, said forming blade during said second phase driving said anvil and partially closed staple to a second anvil position displaced from said first position, said forming blade during said third phase bending said staple to said closed state.

5. A stapler according to claim 4 wherein said forming blade and second means operate reversibly and cyclically, the stapler further comprising means for holding a plurality of staples in said housing and for dispensing one staple at a time to said anvil, each dispensed staple being bendable from open to closed state during one cyclic operation of the stapler.

6. A stapler according to claim 4 further comprising stop means for releasable restraining said anvil at said start position and for supporting said sides of the staple on said anvil while said forming blade is driven from its start position to said partial closure position, said second means being coupled to remove said stop means from supporting said anvil and said sides of said staple when said forming blade moves through said second phase.

7. A stapler according to claim 4 further comprising stop means for releasably supporting said sides of the staple on said anvil while said forming blade is driven from its start position to said partial closure position, said second means being coupled to remove said stop means from supporting said staple sides when said forming blade moves through said second phase.

8. A stapler according to claim 1 wherein said forming blade further comprises a second inclined edge on said top wall of said recess inclined relative to said downward direction, whereby movement of said forming blade during said second stage causes said second inclined edge to cam said crossbar off of said anvil in said transverse direction while said first inclined edge cams said sides of said staple in closed state in said transverse direction.

9. A stapler according to claim 8 where said second inclined edge comprises a bevel in the range of 20° to 70° relative to said downward direction.

10. A stapler according to claim 1 wherein said staple in open state has legs extending downward and coverging toward each other, and wherein said forming blade has first and second sequential phases of movement during said first stage, said forming blade during said first phase driving said anvil and staple in said open state with legs extending downward and converging to a second position displaced from said first position, and said forming blade during said second phase while said anvil remains stationary at its second position bends said staple to said closed state.

11. A stapler according to claim 10 wherein said forming blade further comprises a second inclined edge on said top wall of said recess inclined relative to said downward direction, whereby movement of said forming blade during said second stage causes said second inclined edge to cam said crossbar off of said anvil in said transverse direction while said first inclined edge cams said sides of said staple in closed state in said transverse direction.

12. A stapler according to claim 11 where said second inclined edge comprises a bevel in the range of 20° to 70° relative to said downward direction.

13. A stapler according to claim 10 wherein said second means comprises a trigger having a pivotable part extending outward and exposed from said housing and a drive part coupled to said forming blade.

14. A stapler according to claim 10 wherein said first inclined edge is a bevel in the range of 20° to 70° relative to said downward direction.

15. A stapler according to claim 1 wherein said drive surface further comprises concave grooves for engaging the sides of a staple during said first stage.

16. A stapler according to claim 1 wherein said second means comprises a trigger having a pivotable part extending outward and exposed from said housing and a drive part coupled to said forming blade.

17. A stapler according to claim 1 wherein said first inclined edge is a bevel in the range of 20° to 70° relative to said downward direction.

18. A stapler according to claim 1 whereby said forming blade and second means operate reversibly and cyclically, the stapler further comprising means for holding a plurality of staples in said housing and for dispensing one staple at a time to said anvil, each dispensed staple being bendable from open to closed state during one cyclic operation of the stapler.

19. A surgical stapler operable with a staple that is bendable from an open state which in upright orientation has a horizontal crossbar and generally downward extending pointed legs to a closed state with the legs pointed generally toward each other and with sides of the staple extending generally downward between said crossbar and said legs, the stapler in upright orientation comprising a housing, first means for holding at least one staple in said open state in said housing, an anvil at a first position for receiving a staple from said first means and supporting the crossbar of said staple, a forming blade movable downward through a first stage from start to closure positions and subsequently through a second stage from closure to strip positions, second means for driving said forming blade through said stages, and a stripper for stripping a staple in closed state off said anvil, said stripper movably mounted in said housing and coupled to said second means and comprising a body part and a pair of spaced-apart stripper surfaces inclined relative to said downward direction of said forming blade and situated to engage said sides of the staple, whereby, during movement of the forming blade through said first stage while said anvil remains stationary said drive surface engages and bends a staple about said anvil to said closed state thus forming sides of the staple between its crossbar and legs, and whereby, during movement of said forming blade through said second stage while said anvil remains stationary said stripper surfaces engage and cam said sides of said staple in a direction transverse of said downward direction, thereby stripping said staple in closed state off of said anvil.

20. A surgical stapler operable with a staple that is bendable sequentially from an open state which in upright orientation has a horizontal crossbar and generally downward extending pointed legs to a closed state with legs pointed generally toward each other, the stapler in an upright orientation comprising a housing, first means for holding at least one staple in said open state in said housing, an anvil for receiving a staple from said first means and supporting the crossbar thereof, a forming blade movable in a downward direction sequentially from a start position through a first stage, first phase to a partial closure position, through a first stage, second phase to a closure position, and through a second stage to a strip position, and second means on said housing for driving said forming blade through said stages, said forming blade comprising a body part having a lower portion comprising a drive surface which defines therein an upward extending arched recess having spaced apart side walls joined by a top wall, whereby during movement of the forming blade through said first stage, first phase while said anvil remains stationary said drive surface engages and bends a staple about said anvil to a partially closed state forming sides of the staple between its crossbar and legs with said legs extending downward and converging toward each other, and movement of said forming blade through said second phase displaces said anvil and partially closed staple from said start position to a second position, and during movement of said forming blade through said second stage while said anvil remains stationary at said second position said drive surface bends said staple to said closed state about said anvil.

21. A stapler according to claim 20 wherein said side walls of said recess each comprise at least in part a first edge inclined relative to said downward direction, whereby during movement of the forming blade through said second stage while said anvil remains stationary said inclined edges cam said sides of said staple in a direction transverse of said downward direction for stripping said staple in closed state off of said anvil.

22. A stapler according to claim 20 wherein said forming blade further comprises a second inclined edge on said top wall of said recess inclined relative to said downward direction, whereby movement of said forming blade during said second stage causes said second inclined edge to cam said crossbar off of said anvil in said transverse direction while said first inclined edge cams said sides of said staple in closed state in said transverse direction.

23. A stapler according to claim 20 further comprising stop means for releasably restraining said anvil at said start position and for supporting said sides of the staple on said anvil while said forming blade is driven from its start position to said partial closure position, said second means being coupled to remove said stop means from supporting said anvil and said sides of said staple when said forming blade moves through said second phase.

24. A stapler according to claim 23 wherein said stop means comprises a first stop element positionable adjacent said anvil and a second stop element positionable beneath said crossbar adjacent said anvil.

25. A stapler according to claim 23 wherein said second means comprises a movable trigger having an engagable part extending and exposed from said housing and a drive part coupled to said forming blade.

26. A stapler according to claim 23 wherein said stop means comprises a pair of pin-like elements positionable below the sides of a staple on said anvil.

27. A stapler according to claim 20 further comprising stop means for releasably supporting said sides of the staple on said anvil while said forming blade is driven from its start position to said partial closure position, said second means being coupled to remove said stop means from supporting said staple sides when said forming blade moves through said second phase.

* * * * *

UNITED STATES PATENT AND TRADEMARK OFFICE
CERTIFICATE OF CORRECTION

PATENT NO. : 4,669,647

DATED : June 2, 1987

INVENTOR(S) : Anthony Storace

It is certified that error appears in the above-identified patent and that said Letters Patent is hereby corrected as shown below:

Column 3, line 36, after "cause the" insert --remote end by direct linkage to actuate and drive the--;

line 37, change "mones" to --moves--.

Column 5, line 31, change "17c - 17x" to --17c - 17f--.

Column 7, line 40, change "it" to --is--;

line 49, change "crosssection" to --cross-section--.

Column 8, line 5, change "17a - 17" to --17a - 17f--;

line 16, change "40" to --40a--.

Signed and Sealed this

Third Day of July, 1990

*Attest:*

HARRY F. MANBECK, JR.

*Attesting Officer*  *Commissioner of Patents and Trademarks*